(12) United States Patent
Murase et al.

(10) Patent No.: US 9,220,406 B2
(45) Date of Patent: Dec. 29, 2015

(54) OPHTHALMIC PHOTOGRAPHING APPARATUS AND STORAGE MEDIUM STORING OPHTHALMIC PHOTOGRAPHING PROGRAM

(71) Applicant: NIDEK CO., LTD., Gamagori, Aichi (JP)

(72) Inventors: Yuji Murase, Gamagori (JP); Mitsuo Yamamoto, Gamagori (JP)

(73) Assignee: NIDEK CO., LTD., Aichi (JP)

( * ) Notice: Subject to any disclaimer, the term of this patent is extended or adjusted under 35 U.S.C. 154(b) by 172 days.

(21) Appl. No.: 14/161,739

(22) Filed: Jan. 23, 2014

(65) Prior Publication Data

US 2014/0204338 A1    Jul. 24, 2014

(30) Foreign Application Priority Data

Jan. 23, 2013  (JP) ................................. 2013-010633

(51) Int. Cl.
*A61B 3/14*  (2006.01)
*A61B 3/10*  (2006.01)
*A61B 3/00*  (2006.01)

(52) U.S. Cl.
CPC .............. *A61B 3/102* (2013.01); *A61B 3/0041* (2013.01); *A61B 3/1025* (2013.01); *A61B 3/14* (2013.01)

(58) Field of Classification Search
CPC ...... A61B 3/102; A61B 3/1025; A61B 3/113; A61B 3/14; A61B 3/145
USPC .......................... 351/205, 206, 209, 210, 246
See application file for complete search history.

(56) References Cited

U.S. PATENT DOCUMENTS

| | | | |
|---|---|---|---|
| 8,985,772 B2 * | 3/2015 | Murase | A61B 3/102 351/206 |
| 2008/0024721 A1 | 1/2008 | Ueno et al. | |
| 2010/0110171 A1 | 5/2010 | Satake | |
| 2011/0170062 A1 | 7/2011 | Isogai et al. | |
| 2012/0121158 A1 * | 5/2012 | Sekine | G01N 21/4795 382/131 |
| 2012/0127428 A1 | 5/2012 | Isogai et al. | |

FOREIGN PATENT DOCUMENTS

| | | |
|---|---|---|
| JP | 2008-29467 A | 2/2008 |
| JP | 2010-110392 A | 5/2010 |
| JP | 2011-92702 A | 5/2011 |
| JP | 2011-245183 A | 12/2011 |

* cited by examiner

*Primary Examiner* — Huy K Mai
(74) *Attorney, Agent, or Firm* — Sughrue Mion, PLLC

(57) ABSTRACT

An ophthalmic photographing apparatus includes: an interference optical system configured to acquire a tomographic image of an eye; a processor; and memory storing computer readable instructions, when executed by the processor, causing the ophthalmic photographing apparatus to: control the interference optical system to acquire multiple tomographic images, and store the multiple tomographic images in a storage unit; acquire a composite image based on the multiple tomographic images stored in the storage unit; start a photographing operation for acquiring the multiple tomographic images based on the photographing position; acquire the composite image from the multiple tomographic images which are acquired by the interference optical system and stored in the storage unit until a first operation signal is received during the photographing operation; and transfer a process to a subsequent photographing operation when a second operation signal is received from the operation unit.

11 Claims, 4 Drawing Sheets

OPHTHALMIC PHOTOGRAPHING APPARATUS AND STORAGE MEDIUM STORING OPHTHALMIC PHOTOGRAPHING PROGRAM

CROSS REFERENCE TO RELATED APPLICATION

This application is based upon and claims the benefit of priority of Japanese Patent Application No. 2013-010633 filed on Jan. 23, 2013, the contents of which are incorporated herein by reference in its entirety.

BACKGROUND

The present invention relates to an ophthalmic photographing apparatus which photographs a tomographic image of an eye to be examined and a storage medium which stores an ophthalmic photographing program.

As an ophthalmic photographing apparatus which can non-invasively acquire a tomographic image in a predetermined site (for example, eye fundus and anterior ocular segment) of an eye to be examined, ophthalmic optical coherence tomography (OCT) device using low coherent light has been known (for example, refer to JP-A-2008-29467).

In addition, in the ophthalmic optical coherence tomography, an apparatus has been known which acquires the tomographic image at multiple photographing positions by taking a single photograph and using a scan pattern (for example, a raster scan, a radial scan, a multi-scan and the like) configured to have scans (multiple scanning lines) at different transverse positions (for example, refer to JP-A-2011-92702, and JP-A-2011-245183).

In these apparatuses, in some cases, various noises may be generated in a photographed image. In the related art, when the noises are generated in the photographed image, influences of the randomly generated noises are generally reduced by performing an adding process on multiple photographed images which are photographed in the same region and by averaging pixel values (for example refer to JP-A-2010-110392).

SUMMARY

Incidentally, it is difficult to excellently acquire images in the same region when using an adding method for removing noises of the photographed image, when alignment is insufficiently made between the eye and the apparatus, or when the photographing position is misaligned during the photographing. Therefore, when performing the adding process on these images, the adding process is unlikely to proceed. Consequently, in some cases, it takes time to complete the photographing or the photographing ends in failure. In addition, there is a problem in that the images acquired by the adding process are poor in quality.

In the related art, in order for an examiner to understand this situation, it is necessary to complete the photographing and to confirm the photographed image acquired after a photographing screen is transferred to a confirmation screen or an analysis screen. Since it takes time to complete the photographing, these procedures are very burdensome to the examiner or a subject.

The present invention is made in view of the above-described problems, and a technical object thereof is to provide an ophthalmic photographing apparatus which can shorten a photographing time and can easily acquire an excellent tomographic image.

An aspect of the present invention provides the following arrangements:

An ophthalmic photographing apparatus comprising:

an interference optical system configured to acquire a tomographic image of an eye, the interference optical system including an optical scanner configured to scan the eye by using a light beam emitted from a light source and a detector configured to detect an interference signal between a measurement beam and a reference beam which are emitted from the light source;

a processor; and memory storing computer readable instructions, when executed by the processor, causing the ophthalmic photographing apparatus to:

control the interference optical system to acquire multiple tomographic images based on a photographing position set on the eye, and store the multiple tomographic images in a storage unit;

acquire a composite image by performing a composite process on the multiple tomographic images stored in the storage unit;

receive an operation signal from an operation unit;

start a photographing operation for acquiring the multiple tomographic images based on the photographing position set by the image acquisition unit;

acquire the composite image from the multiple tomographic images which are acquired by the interference optical system and stored in the storage unit until a first operation signal is received from the operation unit during the photographing operation; and transfer a process to a subsequent photographing operation when a second operation signal is received from the operation unit.

It is possible to shorten a photographing time and to easily acquire an excellent tomographic image.

DESCRIPTION OF EXEMPLARY EMBODIMENTS

Figure 1:
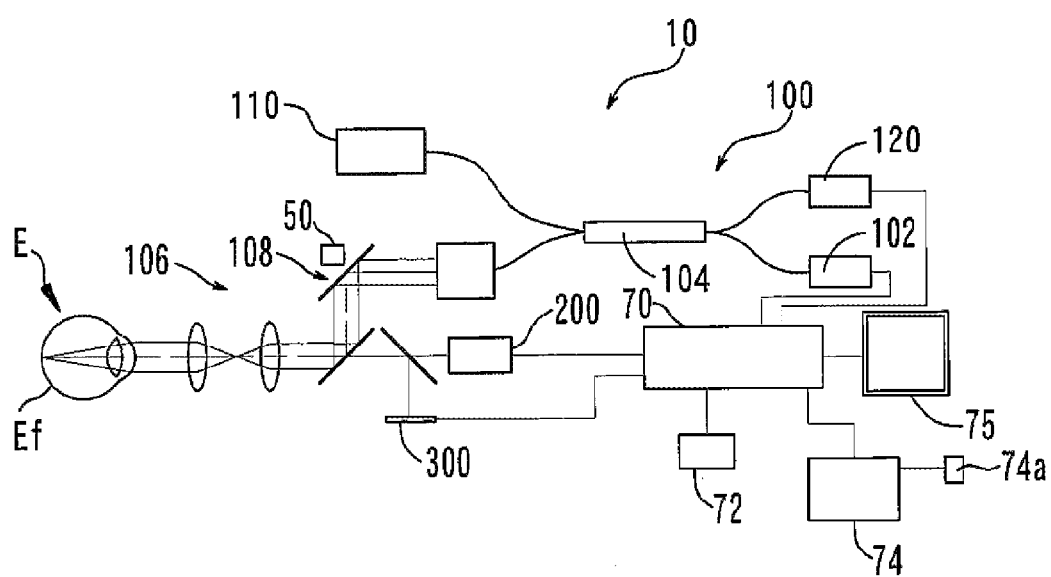
FIG. 1 is a schematic configuration diagram illustrating a configuration of an ophthalmic photographing apparatus according to the present embodiment.

Hereinafter, an embodiment according to the present invention will be described with reference to the drawings. FIGS. 1 to 7 illustrate a configuration of an ophthalmic photographing apparatus according to the present embodiment. In the present embodiment, description will be made so that an axial direction of an eye to be examined (eye E) is a Z-direction, a horizontal direction thereof is an X-direction and a vertical direction thereof is a Y-direction. A surface direction of the eye fundus may be considered as an XY direction.

Overview

An overview of the ophthalmic photographing apparatus according to the embodiment of the present invention will be described. The ophthalmic photographing apparatus (optical coherence tomography device) 10 related to the present embodiment includes an interference optical system 100, a control unit (CPU) 70, an observation optical system 200 and an operation unit (operation device) 74.

The interference optical system 100 has a scanning device (optical scanner) 108 and a detector 120, and acquires a tomographic image of the eye. The optical scanner 108 scans the eye by using a light beam emitted from a light source 102. The detector 120 detects an interference signal between a measurement beam and a reference beam which are emitted from the light source.

The operation unit 74 is operated by an examiner. For example, as the operation unit 74, a user interface such as a mouse 74a, a trackball, a touch panel and the like is used.

The observation optical system 200 has an illumination optical system for illuminating the eye and a light receiving optical system for receiving a reflected beam from the eye. The observation optical system 200 acquires a front image of the eye based on a light receiving signal from the light receiving optical system. For example, a scanning laser ophthalmoscope (SLO) or an eye fundus camera is included therein.

In the present embodiment, the control unit 70 also functions as an image acquisition unit, an image composite unit, a receiving unit, and a transfer unit. As a matter of course, different control units may be respectively configured, or the control units may be configured to be partially shared in use. The receiving means is a configuration for receiving an operation signal from the operation unit 74.

The control unit 70 acquires multiple tomographic images by controlling the interference optical system 100, based on a photographing position set on the eye, and causes a storage unit (memory 72) to store the images. The control unit 70 acquires a composite image by performing a composite process on the multiple tomographic images stored in the memory 72.

For example, the composite image includes an averaged image acquired by performing an averaging process, a super-resolution image acquired by performing super-resolution image processing and a differential image acquired by performing differential image processing.

The control unit 70 starts a photographing operation for acquiring the multiple tomographic images based on the set photographing position. The control unit 70 acquires a composite image from the multiple tomographic images stored in the memory 72 until the first operation signal is received, when receiving a first operation signal during the photographing operation.

Then, when receiving the second operation signal, the control unit 70 is transferred to the subsequent photographing operation.

For example, when the first operation signal is a temporary stop signal, the control unit 70 may temporarily stop a control for storing the tomographic images in the memory 72. In addition, the control unit 70 may acquire the composite image from the multiple tomographic images stored in the memory 72 until the temporary stop signal is received, and may output the acquired composite image.

For example, when the second operation signal is a photographing restart signal (photographing return signal), the control unit 70 may restart the control for storing the tomographic images in the memory 72 as the subsequent photographing operation, and may store the tomographic images in addition to the number of the acquired tomographic images stored in the memory 72 until the first operation signal is received.

In addition, when the second operation signal is a re-photographing signal, the control unit 70 may restart the control for storing the tomographic images in the memory 72 as the subsequent photographing operation, may reset the number of the acquired tomographic images stored in the memory 72 until the first operation signal is received, and may store the tomographic images in the memory 72 again.

The present invention can be applied to a configuration of acquiring tomographic images at multiple photographing positions (transverse positions). That is, the present invention is not limited only to a configuration of acquiring the tomographic images by using a single scan (for example, a line scan, a circle scan or the like). The present invention can also be applied to a configuration of acquiring the tomographic images by using a scan pattern (a multi-scan, a raster scan, a radial scan, a cross-scan and the like) configured to have multiple scans in combination at different photographing positions. For example, the control unit 70 may control the optical scanner at the different multiple photographing positions set on the eye, may scan the eye by using the measurement beam, may acquire the multiple tomographic images at each photographing position, and may store the multiple tomographic images in the memory 72. The control unit 70 may start the photographing operation for acquiring the multiple tomographic images respectively at the set multiple photographing positions. When receiving the first operation signal during the photographing operation, at a first photographing position where the image is being acquired when the first operation signal is received, the control unit 70 may acquire the composite image from the multiple tomographic images at the first photographing position which are stored in the memory 72 until the first operation signal is received.

For example, in this case, a photographing position change signal can be applied as the second operation signal. When the second operation signal is the photographing position change signal, the control unit 70 may change a position for acquiring the tomographic images from the first photographing position to the second photographing position, as the subsequent photographing operation. Then, the control unit 70 may start the photographing operation for acquiring the tomographic images at the second photographing position.

In this case, a configuration may be made so that the first operation signal and the second operation signal are shared in use. For example, when the second operation signal is the photographing position change signal, if the control unit 70 receives the photographing position change signal during the photographing operation, the control unit 70 may change the photographing position to the subsequent photographing position without the temporary stop of the photographing.

In the above-described ophthalmic photographing apparatus, a tracking control is performed. For example, the control unit 70 may set a predetermined front image as a reference image, in the front images acquired by the observation optical system 200. The control unit 70 detects deviation between the reference image and other front images by image processing. The control unit 70 may control a drive of the optical scanner 108 based on the detection result, and may acquire the multiple tomographic images at the set photographing position. For example, other front images include a configuration of using the front image when acquiring the tomographic image.

The present embodiment is not limited to the apparatus in the above-described embodiment. For example, ophthalmic photographing software (program) for functioning as in the above-described embodiment may be supplied to a system or an apparatus via a network or various storage media. Then, the program can be read out and executed by a computer (for example, CPU or the like) of the system or the apparatus.

For example, the ophthalmic photographing program may be executed in a control device for controlling an operation of the ophthalmic photographing apparatus. In this case, the ophthalmic photographing program is executed by a processor of the control device. In this manner, the program causes the control device to execute a process for the ophthalmic photographing apparatus, the process including: an image acquisition step in which multiple tomographic images are acquired by controlling the interference optical system 100, based on the photographing position set on the eye; a control step in which the photographing operation in the image acquisition step is started, and the composite image is acquired from the multiple tomographic images stored in the memory 72 until the first operation signal is received, when the first operation signal is received by the receiving unit for receiving the operation signal from the operation unit 74 during the photographing operation; and a transfer step in which when the second operation signal is received by the receiving unit, the process is transferred to the subsequent photographing operation using the image acquisition step.

Embodiment

Hereinafter, the present embodiment will be described with reference to the drawings. FIG. 1 is a schematic configuration diagram illustrating a configuration of the ophthalmic photographing apparatus according to the present embodiment. In the following description, as the ophthalmic photographing apparatus, an eye fundus photographing apparatus for photographing an eye fundus of an eye will be described as an example. As a matter of course, without being limited to the eye fundus photographing apparatus, the ophthalmic photographing apparatus includes an anterior ocular segment photographing apparatus for photographing an anterior ocular segment of the eye. In the present embodiment, description will be made so that the axial direction of the eye (eye E) is the Z-direction, the horizontal direction thereof is the X-direction and the vertical direction thereof is the Y-direction. The surface direction of the eye fundus may be considered as the XY direction.

The schematic configuration of the apparatus will be described. The apparatus is an optical coherence tomography device (OCT device) 10 for photographing a tomographic image of an eye fundus Ef of an eye E. The OCT device 10 includes an interference optical system (OCT optical system) 100, a front observation optical system 200, an ocular fixation target projection unit 300 and an arithmetic control unit (CPU) 70.

The OCT optical system 100 emits a measurement beam to the eye fundus. The OCT optical system 100 detects an interference state between the measurement beam reflected from the eye fundus and a reference beam by using a light receiving element (detector 120). The OCT optical system 100 includes a light emitting position change unit (for example, the optical scanner 108 and the ocular fixation target projection unit 300) which changes a light emitting position of the measurement beam on the eye fundus Ef, in order to change the photographing position on the eye fundus Ef. The control unit 70 controls the operation of the light emitting position change unit based on the set photographing position information, and acquires the tomographic image based on a light receiving signal from the detector 120.

OCT Optical System

The OCT optical system 100 has a device configuration of so-called ophthalmic optical coherence tomography (OCT), and photographs the tomographic image of the eye E. The OCT optical system 100 splits a light beam emitted from a measurement beam source 102 into the measurement beam (sample beam) and the reference beam by using a coupler (beam splitter) 104. Then, the OCT optical system 100 guides the measurement beam to the eye fundus Ef of the eye E by using a measurement optical system 106, and additionally guides the reference beam to a reference optical system 110. Thereafter, the OCT optical system 100 causes the detector (light receiving element) 120 to receive an interference beam in which the measurement beam reflected on the eye fundus Ef is synthesized with the reference beam.

The detector 120 detects an interference state between the measurement beam and the reference beam. In a case of a Fourier-domain OCT, spectral intensity of the interference beam is detected by the detector 120, and a depth profile (A scan signal) is acquired in a predetermined range by performing Fourier transform on spectral intensity data. For example, any one of a spectral-domain OCT (SD-OCT), a swept-source OCT (SS-OCT) and a time-domain OCT (TD-OCT) may be employed in the detector 120.

The optical scanner 108 scans the eye fundus of the eye by using the beam emitted from the measurement light source. For example, the optical scanner 108 scans the eye fundus two-dimensionally (in the XY direction (transverse direction)) by using the measurement beam. The optical scanner 108 is arranged at a substantially conjugating position with the pupil of the eye. For example, the optical scanner 108 is configured to have two galvanometer mirrors, and a reflection angle thereof is arbitrarily adjusted by a drive mechanism 50.

In this manner, a light flux emitted from the light source 102 is caused to have a changed reflection (travelling) direction, and scans the eye fundus in an arbitrary direction. In this manner, the photographing position on the eye fundus Ef is changed. The optical scanner 108 may employ any configuration which causes the light beam to be polarized. For example, in addition to a reflection mirror (a galvanometer mirror, a polygon mirror and a resonant scanner), an acousto-optical modulator (AOM) which changes the travelling (polarizing) direction of the light beam may be used.

The reference optical system 110 generates the reference beam which is synthesized with the reflected beam acquired by the reflection of the measurement beam on the eye fundus Ef. The reference optical system 110 may be a Michelson type or a Mach-Zehnder type. For example, the reference optical system 110 may be formed from a reflection optical system (for example, a reference mirror). The light beam from the coupler 104 is reflected by the reflection optical system. In this manner, the light beam is caused to return to the coupler 104 again, and is guided to the detector 120. As another example, the reference optical system 110 may be formed from a transmission optical system (for example, an optical fiber). The light beam from the coupler 104 is not caused to return to the coupler 104, but is transmitted therethrough. In this manner, the light beam is guided to the detector 120.

The reference optical system 110 has a configuration for changing a difference in lengths of the optical paths for the measurement beam and the reference beam by moving an optical member in a path for the reference beam. For example, the reference mirror is moved in an optical axis direction. The configuration for changing the difference in lengths of the optical paths may be arranged in a path for the measurement beam of the measurement optical system 106.

Front Observation Optical System

The front observation optical system (front image observation device) 200 is disposed to acquire a front image of the eye fundus Ef. For example, the observation optical system 200 includes an optical scanner which scans the eye fundus two-dimensionally by using the measurement beam (for example, an infrared beam) emitted from the light source, and a second light receiving element which receives the light beam reflected on the eye fundus via a confocal aperture arranged at a substantially conjugate position with the eye fundus. The observation optical system 200 has an apparatus configuration of a so-called ophthalmic scanning laser ophthalmoscope (SLO).

As the configuration of the observation optical system 200, a configuration of a so-called eye fundus camera type may be adopted. In addition, the OCT optical system 100 may also function as the observation optical system 200. That is, the front image may be acquired by using data for forming the tomographic image which is two-dimensionally acquired (for example, an integrated image in a depth direction of a three-dimensional tomographic image, integrated values of spectral data at each position of XY, brightness data at each position of XY in a constant depth direction, a retinal cortex image and the like).

When the observation optical system 200 is the SLO or the eye fundus camera, the control unit 70 performs alignment (matching) on the front image acquired by the observation optical system 200 and the front image acquired by the interference optical system 100 (for example, an OCT front image based on three-dimensional image data (for example, integrated image)). In this manner, the tomographic image acquired by the interference optical system 100 is associated with the front image acquired by the observation optical system 200.

Ocular Fixation Target Projection Unit

The ocular fixation target projection unit 300 has an optical system for inducing a viewing direction of the eye E. The projection unit 300 has an ocular fixation target presented to the eye E, and can induce the eye E in multiple directions.

For example, the ocular fixation target projection unit 300 has a visible light source for emitting a visible light beam, and two-dimensionally changes a presentation position of an ocular target. In this manner, a viewing direction is changed and consequently a photographing region is changed. For example, if an ocular fixation target is presented from the same direction as that of an optical axis in photographing, a central portion of the eye fundus is set as the photographing region. In addition, if the ocular fixation target is presented upward with respect to the optical axis in photographing, an upper portion of the eye fundus is set as the photographing region. That is, the photographing region is changed depending on positions of the ocular target with respect to the optical axis in photographing.

For example, as the ocular fixation target projection unit 300, various configurations can be considered such as a configuration where an ocular fixation position is adjusted by a lighting position of LEDs arrayed in a matrix shape, and a configuration where the optical scanner is caused to scan the ocular fixation position by using the light beam emitted from the light source and the ocular fixation position is adjusted by a lighting control of the light source. In addition, the projection unit 300 may be an internal fixation lamp type or an external fixation lamp type.

Control Unit

The control unit 70 includes a CPU (processor), a RAM, a ROM and the like. The CPU of the control unit 70 controls the ophthalmic photographing apparatus 10. The RAM temporarily stores various information items. The ROM of the control unit 70 stores various programs for controlling operations of the ophthalmic photographing apparatus 10, initial values and the like.

A nonvolatile memory (storage unit) 72, an operation unit (control unit) 74 and a display unit (monitor) 75 are electrically connected to the control unit 70. The nonvolatile memory 72 is a non-fugitive storage medium which can hold stored contents even when power supply is cut off. For example, a hard disk drive, a flash ROM, and a USB memory which is detachably attached to the ophthalmic photographing apparatus 10 can be used as the nonvolatile memory 72. A photographing control program for controlling the ophthalmic photographing apparatus 10 photographing the front image and the tomographic image is stored in the nonvolatile memory 72. In addition, the nonvolatile memory 72 stores various information items relating to the photographing such as the two-dimensionally photographed tomographic images, the three-dimensional images, the front images, and information on the photographing position of the tomographic image. Various operation instructions are input to the operation unit 74 by an examiner.

The operation unit 74 outputs a signal corresponding to an input operation instruction to the control unit 70. For example, the operation unit 74 may employ at least any one of a mouse, a joystick, a keyboard, a touch panel and the like.

The monitor 75 may be a display mounted on a main body of the ophthalmic photographing apparatus 10 or a display connected to the main body. A display of a personal computer (hereinafter, referred to as a "PC") may be used. A plurality of displays may be used together. In addition, the monitor 75 may be a touch panel. When the monitor 75 is the touch panel, the monitor 75 functions as the operation unit. The monitor 75 displays various images including the tomographic images and the front images which are photographed by the ophthalmic photographing apparatus 10.

The control unit 70 may be configured to have a plurality of control units (that is, a plurality of processors). For example, the control unit 70 of the ophthalmic photographing apparatus 10 may be configured to have a setting control unit disposed in the PC and an operation control unit for controlling the operation of the OCT optical system 100. In this case, for example, the setting control unit of the PC may receive the operation signal of the operation unit 74 connected to the PC, and may instruct various control operations to the operation control unit, based on the received operation signal. That is, the setting control unit serves as a receiving unit for receiving the operation signal from the operation unit. The operation control unit may control photographing operations performed by each configuration of the ophthalmic photographing apparatus 10 according to the instruction from the setting control unit. In addition, the process of generating (acquiring) the image based on a light receiving signal may be performed by either the operation control unit or the setting control unit. In the present embodiment, the control unit 70 also functions as an image acquisition unit, an image composite unit, the receiving unit, and a transfer unit. As a matter of course, different control units may be respectively configured, or the control units may be configured to be partially shared in use.

The mouse 74a includes a sensor for detecting a movement signal when a main body of the mouse 74a is two-dimensionally moved by an examiner's hand, two right and left mouse buttons for detecting whether there is pressing by the examiner's hand, and a wheel mechanism which is rotatable in a back and forth direction between two right and left mouse buttons.

The control unit 70 acquires the tomographic image by image processing based on the light receiving signal output from the detector 120 of the OCT optical system 100, and acquires the front image based on the light receiving signal output from the light receiving element of the front observation optical system 200. In addition, the control unit 70 controls the ocular fixation target projection unit 300 changing the ocular fixation position.

Control Operation

A control operation in the apparatus including the above-described configurations will be described. The control unit 70 executes a process according to a control program stored in the memory 72. An examiner instructs a subject to gaze at an ocular fixation target of the ocular fixation target projection unit 300. Then, while using the monitor 75 to check an observation image of the anterior ocular segment which is photographed by an anterior ocular segment observation camera (not illustrated), the examiner performs an alignment operation so that the optical axis in measuring is positioned in the center of the pupil of the subject by using the operation unit 74 (for example, a joystick (not illustrated)).

Then, the control unit 70 controls the drive of the optical scanner 108 scanning the eye fundus in a predetermined direction by using the measurement beam. The control unit 70 acquires the light receiving signal corresponding to a predetermined scanning region, from an output signal output from the detector 120 during the scanning, thereby forming the tomographic image. In addition, the control unit 70 controls the OCT optical system 100 acquiring the tomographic image, and controls the observation optical system 200 acquiring the front image of the eye fundus. Then, the control unit 70, whenever necessary, acquires the tomographic image by using the OCT optical system 100, and acquires the front image of the eye fundus by using the observation optical system 200.

Hereinafter, in the present embodiment, a case of acquiring the tomographic images by using a scan pattern (a multi-scan, a raster scan, a radial scan, a cross-scan and the like) configured to have multiple scans in combination at different transverse positions will be described as an example. The present invention can also be applied to a single scan (for example, a line scan, a circle scan or the like).

Hereinafter, as the scan pattern configured to have the multiple scans in combination, the multi-scan will be described as an example. For example, as the multi-scan of the present embodiment, a multi-scan configured to have five vertical scanning lines and five horizontal scanning lines will be described as an example. As a matter of course, the number of scanning lines can be changed without being limited thereto.

Figure 2:
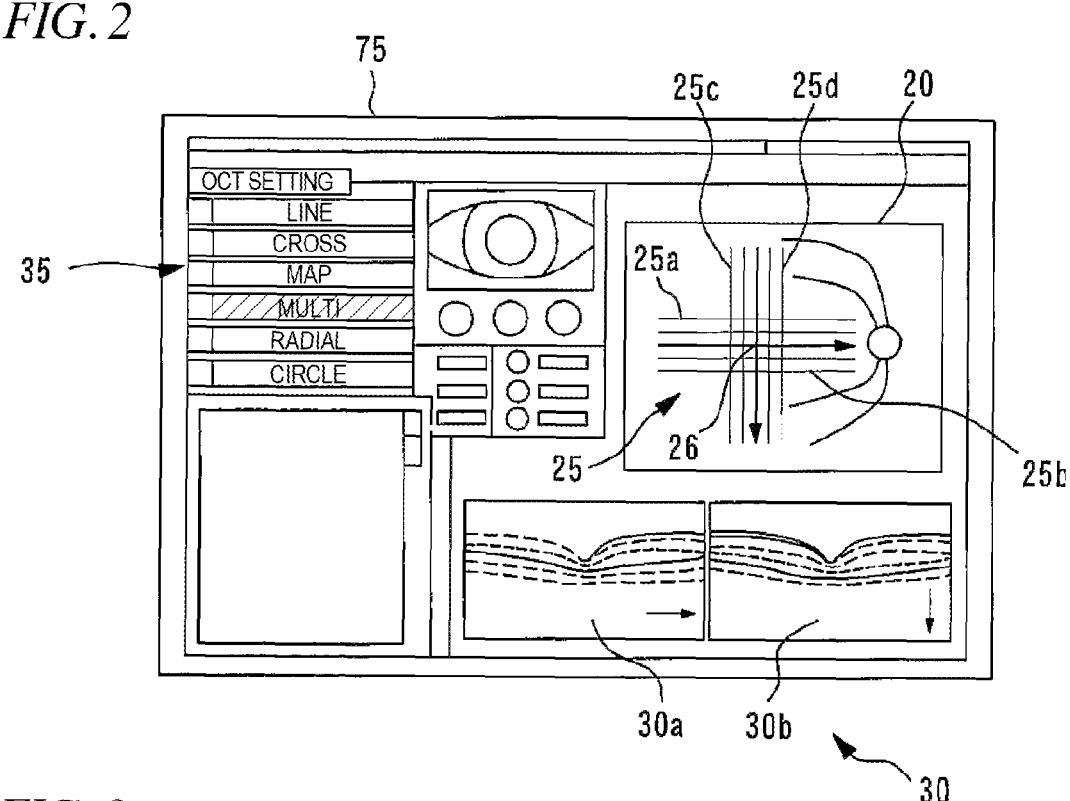
FIG. 2 illustrates an example of a photographing screen displayed on a monitor in a case of photographing by using a multi-scan.

FIG. 2 illustrates an example of a photographing screen displayed on the monitor 75 in a case of multi-scan photographing. The control unit 70 displays a front image 20 acquired by the observation optical system 200, an indicator 25 and a tomographic image 30, on the monitor 75. The indicator 25 indicates a measurement position (acquisition position) of the tomographic image on the front image 20, and the scan pattern. That is, if the scan pattern is changed, the control unit 70 changes a display pattern of the indicator, based on the changed scan pattern. The indicator 25 is electrically superimposed and displayed on the front image displayed on the monitor 75.

For example, as the tomographic image 30, a first tomographic image 30a and a second tomographic image 30b are displayed on the monitor 75. For example, the first tomographic image 30a indicates a tomographic image acquired at a cutting position passing through the indicator 25 in the horizontal direction (X-direction). In addition, for example, the second tomographic image 30b indicates a tomographic image acquired at the cutting position passing through the indicator 25 in the vertical direction (Y-direction).

In the present embodiment, as initial setting in multi-scan photographing, the tomographic images displayed on the photographing screen of the first tomographic image 30a and the second tomographic image 30b are configured to display the tomographic images of the horizontal scan and the vertical scan at a center position 26 of the multi-scan. As a matter of course, the images acquired at different scanning positions may be displayed during the photographing. In addition, the tomographic images displayed on the first tomographic image 30a and the second tomographic image 30b can be changed by the operation of the operation unit. For example, if the mouse 74a is operated to select the scanning line at a position which the examiner wants to confirm on the tomographic image, the display is changed to the tomographic image acquired by the selected scanning line.

Hereinafter, a photographing method of the tomographic image will be described. As illustrated in FIG. 2, if the tomographic image and the front image are displayed on the same screen, the examiner sets a position of the tomographic image which the examiner wants to photograph by using the front image on the monitor 75 which can be observed in real time. Here, the examiner uses the mouse 74a to perform a drag operation, and moves the indicator 25 to the front image to set the scanning position.

If the indicator 25 is moved to the front image 20 by the examiner, the control unit 70 sets the position for the scanning whenever necessary, and acquires the tomographic image at the scanning position corresponding thereto. Then, the control unit 70 displays the acquired tomographic image on the display screen of the monitor 75 whenever necessary. In addition, the control unit 70 changes the scanning position of the measurement beam, based on the operation signal output from the mouse 74a, and displays the indicator 25 at the display position corresponding to the changed scanning position. The scanning position is changed and a scan pattern setting section 35 is selected by the operation unit 74, thereby enabling the scan pattern to be changed.

If the scan pattern or the scanning position is set by the examiner and a photographing switch (not illustrated) is selected, the control unit 70 acquires the front image and the tomographic image, based on the set scanning position.

The control unit 70 causes the memory 72 to store the front image acquired when starting the multi-scan photographing and information of the scanning position of the multi-scan which is set on the front image. The front image is used in the tracking control for re-photographing (to be described in detail below).

In addition, based on the display position of the indicator 25 set on the front image 20, the control unit 70 drives the optical scanner 108 to scan the eye fundus by using the measurement beam so as to acquire the tomographic image of the eye fundus which corresponds to the position of the indicator 25. A relationship between the display position of the indicator 25 (coordinate position on the monitor 75) and the scanning position of the measurement beam used by the optical scanner 108 is predetermined. Accordingly, the control unit 70 appropriately drives and controls two galvanometers of the optical scanner 108 so that the measurement beam is used in scanning for a scan range corresponding to the display position of the set indicator 25.

When acquiring the tomographic image, if the photographing is performed by using the scan pattern configured to have the multiple scans, the control unit 70 sequentially acquires the tomographic images by each scan. For example, when the photographing is performed by the above-described multi-scan, after the photographing is completed in all the horizontal scanning lines, the photographing is performed in all the vertical scanning lines. For example, when the photographing is performed in each horizontal scanning line, the photographing is performed sequentially downward from the scanning line located at the upper end. That is, the horizontal photographing is performed sequentially from the upper end indicator 25a to the lower end indicator 25b in the horizontal direction of the indicator 25.

At this time, in order to acquire one tomographic image (B scan image) which suppresses a noise component in each scanning line, the photographing of the tomographic image is performed in each scanning line multiple times. For example, the control unit 70 performs the photographing at the position of the upper end indicator 25a multiple times, and generates multiple tomographic images to be stored in the memory 72. Here, the control unit 70, whenever necessary, adds and averages (performs averaging process) the multiple tomographic images to be stored in the memory 72. In this manner, an averaged image is acquired from the multiple tomographic images at each scanning line.

More specifically, with regard to the set scanning position, the control unit 70 first uses the optical scanner 108 to scan a predetermined scanning region (photographing position) by using the measurement beam multiple times, so that the tomographic images can be acquired to be the set multiple frame number of tomographic images (the number to be used in the averaging process). Then, the control unit 70 generates the multiple frame number of tomographic images (the number n (n≥2)) in the same scanning positional region. The control unit 70 causes the memory 72 to store the multiple generated tomographic images. The control unit 70 repeatedly acquires the front image while acquiring the multiple tomographic images, whenever necessary. This control allows the control unit 70 to monitor the movement of the eye while continuously acquiring the tomographic images. That is, the control unit 70 performs the tracking control (to be described in detail below).

Then, the control unit 70, whenever necessary, performs the averaging process on the tomographic images stored in the memory 72. When the multiple frame number of tomographic images used in the averaging process reaches the predetermined number, the control unit 70 completes the photographing at the photographing position, and the photographing position is transferred to the photographing position of the subsequent scanning line. The frame number of tomographic images used in the averaging process may be configured to be set for each scan pattern in advance. As a matter of course, a configuration may be made so that the examiner can arbitrarily set the frame number.

Here, the averaging process will be described. For example, the control unit 70 performs the averaging process on the multiple tomographic images acquired by the OCT optical system 100, thereby acquiring the averaged image. The control unit 70 sets the tomographic image initially acquired (stored in the memory 72) as the reference image at the position of each scanning line, for each scanning line, and performs the averaging process. The control unit 70 detects deviation between the reference image and the other multiple tomographic images by image processing for each tomographic image acquired at the position of each scanning line. Then, based on a deviation detection result thereof, the control unit 70 performs a determination process as to whether to perform the adding process, corrects the deviation between the reference image and each tomographic image, and performs the adding process on the multiple tomographic images with respect to the reference image. In the present embodiment, the reference image is set to be the front image initially acquired (most recently photographed image), but the present embodiment is not limited thereto. For example, the tomographic image used as a reference in the adding process within the multiple tomographic images may be set to be the reference image.

The control unit 70 sequentially performs the averaging process on the tomographic images with respect to the reference image. Then, the control unit 70 detects a deviation amount between each tomographic image and the reference image for each tomographic image, and performs alignment of each tomographic image with respect to the reference image. That is, the control unit 70 compares the reference image with each tomographic image, and detects a positional deviation direction and a positional deviation amount of each tomographic image with respect to the reference image, for each tomographic image by image processing.

As a detection method of the deviation amount, it is possible to use various image processing methods (a method of using various correlation functions, a method of using the Fourier transform and a method based on matching of feature points).

For example, a method can be considered which detects the positional deviation direction and the positional deviation amount between both data items acquired when a predetermined reference image (initially acquired tomographic image) or a target image (tomographic image other than the reference image) is caused to be position-deviated one pixel by one pixel, the reference image is compared with the target image, and both data items coincide with each other most (when the correlation is the highest). In addition, a method can be considered which detects the positional deviation direction and the positional deviation amount between extracted feature points by extracting the feature points which are common to the predetermined reference image and the target image.

In the present embodiment, while each front image is shifted with respect to the reference image one pixel by one pixel, a correlation value is subsequently calculated (as the value increases, the correlation between the images becomes higher (up to the maximum 1)). Then, the control unit 70 calculates the correlation value by setting a displacement amount of the pixel when the correlation value is the maximum to be the positional deviation amount and by setting the displaced direction to be the positional deviation direction.

As a determination method, the correlation value calculated when detecting the deviation may be used to perform the determination. For example, when the correlation value is smaller than a predetermined threshold value (for example, 0.4), the correlation value is excluded from a target of the tomographic image used in the averaging process. That is, when the correlation value is small, there is a high probability that in the reference image and the tomographic image, the photographing region greatly varies due to an involuntary eye movement or the deviation between the apparatus and the eye. The method of determining whether or not the image used in the averaging process is a suitable image is not limited thereto. For example, the tomographic image in which the detected positional deviation amount is outside a permissible range may be excluded from the target of the averaging process. In addition, for example, a configuration may be made in view of the deviation amount between the front images. For example, the tomographic image in which the positional deviation amount of the front image when the tomographic image is acquired is outside the permissible range may be excluded from the targets of the averaging process.

As described above, the positional deviation amount and the positional deviation direction are detected to determine whether or not the image is the suitable image used in the averaging process. Then, the control unit 70 displaces each front image to the reference image respectively by the positional deviation amount so as to correct the positional deviation of the image which is determined to be the suitable image used in the averaging process. Then, after correcting the positional deviation, the control unit 70 adds pixel values of the tomographic image to the reference image.

In this manner, the multiple tomographic images are used in each scanning line to perform the averaging process, thereby improving an image quality of the acquired tomographic image.

After completing the horizontal photographing, similar to the horizontal photographing, the photographing is performed in each vertical scanning line. For example, when performing the photographing in each vertical scanning line, the photographing is performed sequentially rightward from the scanning line located at the left end. That is, the vertical photographing is performed sequentially from the left end indicator 25c to the right end indicator 25d in the vertical direction of the indicator 25. The photographing order is not limited to the above-described manner. For example, after completing the photographing in the vertical scanning lines, the photographing may be configured to be performed in the horizontal scanning lines. In addition, the photographing may be configured to be alternately performed in the vertical and horizontal scanning lines. Alternatively, the photographing may be configured to be switched over between the vertical and horizontal scanning lines every multiple photographing processes.

If the photographing is completed in the manner as described above, the control unit 70 causes the memory 72 to store the acquired tomographic image.

Figure 3:
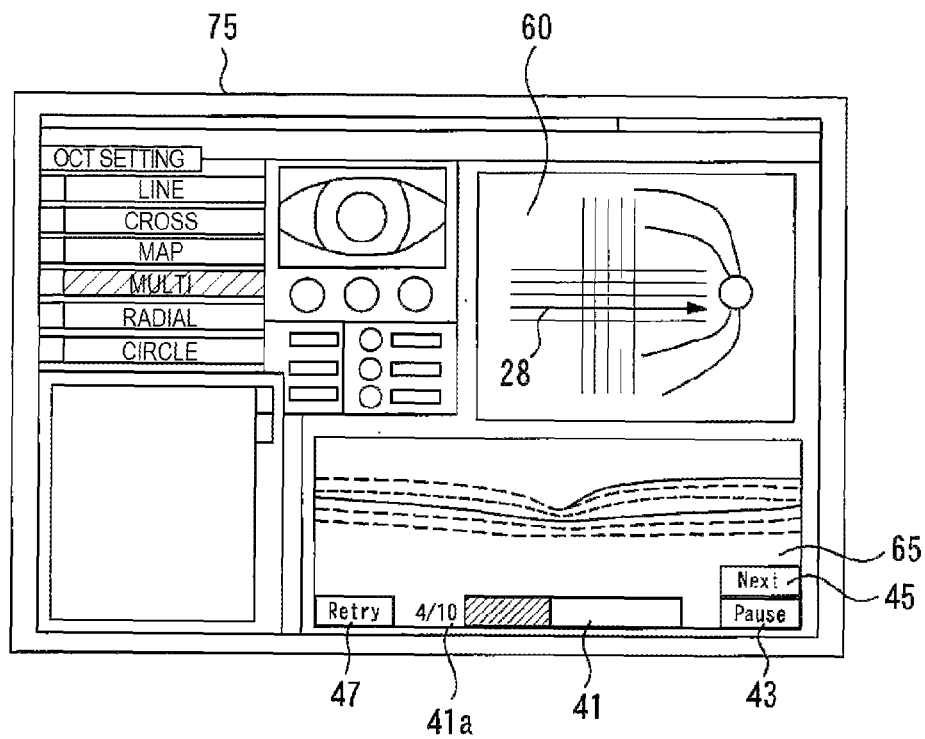
FIG. 3 illustrates an example of a photographing screen which acquires multiple tomographic images at a predetermined photographing position.

The present invention is configured to enable various operations during the photographing of the tomographic image. Hereinafter, the operations during the photographing of the tomographic image will be described. FIG. 3 illustrates an example of the photographing screen which acquires the multiple tomographic images at a predetermined photographing position.

If the scan pattern and the scanning position are set and the photographing is started, the control unit 70 starts the photographing for acquiring the multiple tomographic images at the photographing position of each scan pattern. At this time, when the front image deviates from the scanning position (photographing position) due to the involuntary movement of the eye, in order to acquire the tomographic image at the position which is the same as the position set as the scanning position, a control for correcting the scanning position (tracking control) is required.

Hereinafter, the tracking control will be described. The control unit 70 uses the front image acquired when starting the photographing in the multi-scan stored in the memory 72 and the scanning position information of the multi-scan set on the front image, thereby correcting the scanning position when acquiring the multiple tomographic images. The control unit 70 first compares the front image stored in the memory 72 with the currently displayed front image. The control unit 70 detects (calculates) the positional deviation direction and the positional deviation amount of the currently displayed front image with respect to the front image acquired when starting the photographing in the multi-scan by image processing.

The control unit 70 sets the front image data acquired when starting the photographing in the multi-scan to be the reference image, and calculates the positional deviation between the reference image and the front image acquired in real time. In this manner, it is possible to acquire the positional deviation information with respect to the front image acquired when starting the photographing in the multi-scan.

If the positional deviation is detected in the manner as described above, the control unit 70 appropriately drives and controls two galvanometers of the optical scanner 108 so as to correct the positional deviation between the position of the scanning line 28 when performing the photographing in the past and the position of the current scanning line 28. This corrects the scanning position. In this manner, even when the eye is deviated, the scanning position is corrected to always acquire the tomographic image at the site which is the same as the site in which the photographing position is set. Accordingly, the number of tomographic images which can be used in the averaging process is increased, thereby leading to the improvement in the image quality of the acquired tomographic image. In addition, a probability of photographing the site which is different from the photographing position selected by the examiner is decreased, thereby leading to reduction of mistakes in acquiring the tomographic image.

In the above-described tracking control, as a method of detecting the positional deviation between two images, similar to the above-described averaging process, various image processing methods (a method of using various correlation functions, a method of using the Fourier transform and a method based on matching of feature points) can be used.

As illustrated in FIG. 3, if the scan pattern and the scanning position are set to start the photographing, the photographing of the multiple tomographic images is started at the photographing position of each scan pattern.

For example, a front image 60 and a tomographic image 65 are displayed on a monitor 75. The front image 60 displays the currently acquiring front image. The tomographic image 65 displays a tomographic image (tomographic image in which the averaging process is not performed) acquired at a position of a scanning line 28 within the multi-scan configured to have the multiple scanning lines. That is, the scanning line 28 indicates the photographing position of the current tomographic image within each scan line configuring the multi-scan.

In addition, a parameter 41, a numerical display 41a, a "Pause" switch 43, a "Next" switch 45 and a "Retry" switch 47 are displayed on the screen.

The parameter 41 indicates the frame number of tomographic images used in the averaging process. The parameter 41 is used in order to understand a progress of the averaging process. For example, the parameter 41 in the scanning line 28 is configured so as to graphically display the frame number of tomographic images in which the averaging process is performed. That is, the control unit 70 increases the frame number of the averaged tomographic images in the scanning line 28 and increases a shaded portion (hatched portion) of the parameter 41. In addition, the numerical display 41a is configured so as to numerically display the frame number of tomographic images in which the averaging process is performed. For example, when the frame number of acquired tomographic images at the photographing position in each scanning line represents 10 frames, and if the frame number of tomographic images in which the averaging process is performed represents four frames, the control unit 70 displays 4/10 on the numerical display 41*a*.

The "Pause" switch 43 is used in order to temporarily stop the control for storing the tomographic images at the photographing position where the tomographic image is being acquired (to be described in detail below). The "Next" switch 45 is used in order to complete the photographing at the photographing position where the tomographic image is being acquired and to transfer the process to the subsequent photographing operation (to be described in detail below). The "Retry" switch 47 is used in order to restart the control for storing the tomographic images at the photographing position where the tomographic image is being acquired. Accordingly, the tomographic images stored in the memory 72 at the photographing position the tomographic image is being acquired are deleted (to be described in detail below).

If the photographing is started, the control unit 70 acquires the multiple tomographic images based on the set photographing position, and causes the memory 72 to store the tomographic images. The control unit 70 acquires the composite image from the multiple tomographic images stored in the memory 72 until the first operation signal is received, when receiving the first operation signal during the photographing operation. In addition, the control unit 70 transfers the process to the subsequent photographing operation when receiving the second operation signal.

For example, the examiner confirms the parameter 41 or the numerical display 41*a* in the scanning line 28. When the progress of the averaging process is slow or stopped, the examiner operates the operation unit 74 to select the "Pause" switch 43. If the examiner operates the operation unit 74 to select the "Pause" switch 43 during the acquisition of the multiple tomographic images in the scanning line 28, a temporary stop signal is output. If the temporary stop signal is received, the control unit 70 temporarily stops the control for storing the tomographic images in the memory 72. The control unit 70 acquires the composite images from the multiple tomographic images stored in the memory 72 until the temporary stop signal is received, and outputs the acquired composite image. In the present embodiment, as the composite image, the averaged image acquired by performing the averaging process on the multiple tomographic images is acquired. The present embodiment adopts the configuration of using the averaged image as the composite image, but is not limited thereto. For example, the composite image includes a super-resolution image acquired by performing super-resolution image processing (for example, refer to JP-A-2013-034658) and a differential image acquired by performing differential image processing.

Figure 4:
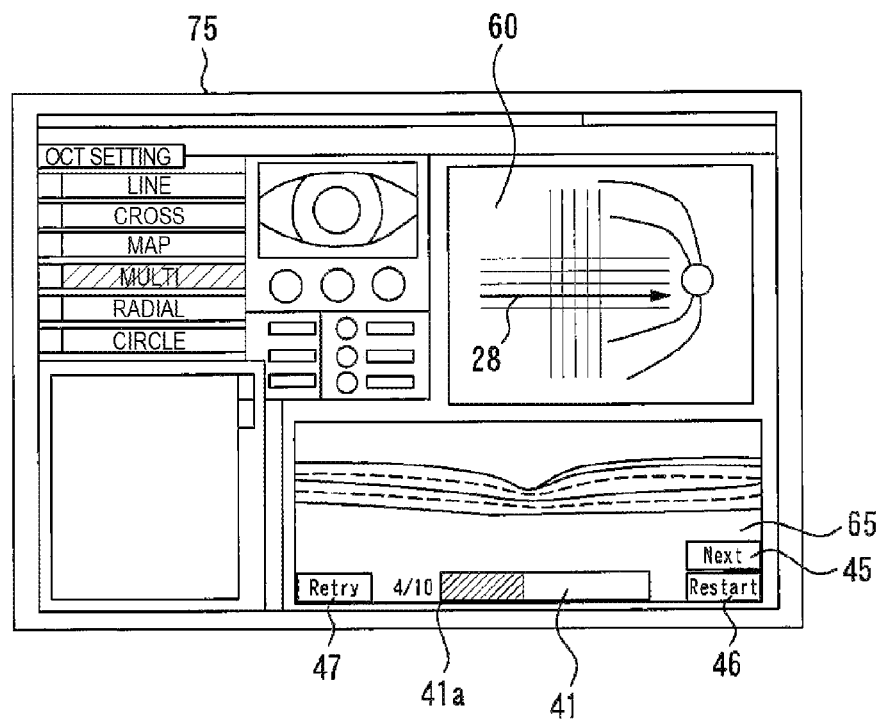
FIG. 4 illustrates an example of a photographing screen during a temporary stop.

The control unit 70 performs the averaging process on the tomographic images stored in the memory 72 in the scanning line 28, and acquires the averaged image. The control unit 70 displays the acquired averaged image on the monitor 75. FIG. 4 illustrates an example of the photographing screen during the temporary stop.

The control unit 70 changes the display switch from the "Pause" switch 43 to a "Restart" switch 46 on the monitor 75. The "Restart" switch 46 is used in order to start the control for storing the tomographic images in the memory 72 from the temporary stop state. In addition, the tomographic image 65 displays the averaged image acquired by performing the averaging process on the tomographic images acquired until the temporary stop in the scanning line 28. Therefore, as compared to the tomographic image 65 in FIG. 3, the tomographic image 65 in FIG. 4 displays the tomographic image having noises removed (tomographic image having fewer dotted portions).

Here, for example, confirming the averaged image, the examiner can confirm the reason why the photographing state is not satisfactory when the progress of the averaging process is slow or stopped. That is, the examiner can confirm an adjustment state of each member in the apparatus, an alignment state between the apparatus and the eye, and an eyelid opening state of the eye. The examiner adjusts the state of each member in the apparatus, the alignment between the apparatus and the eye, and the state of the eye, thereby improving the photographing state. In this manner, it is possible to temporarily stop the photographing of the tomographic image and to confine the tomographic image during the photographing (the averaged image). Accordingly, it is possible to easily succeed in the photographing. As a matter of course, the present invention can be applied to a case where regardless of the quality of the photographing state, the temporary stop is performed so as to confirm the tomographic image for photographing even during the acquisition of the tomographic image. That is, various adjustment procedures are not necessarily required after the temporary stop.

Then, the examiner confirms the averaged image, operates the operation unit 74, and selects any one of the "Next" switch 45, the "Restart" switch 46 and the "Retry" switch 47 to transfer the process to the subsequent photographing operation.

Figure 5:
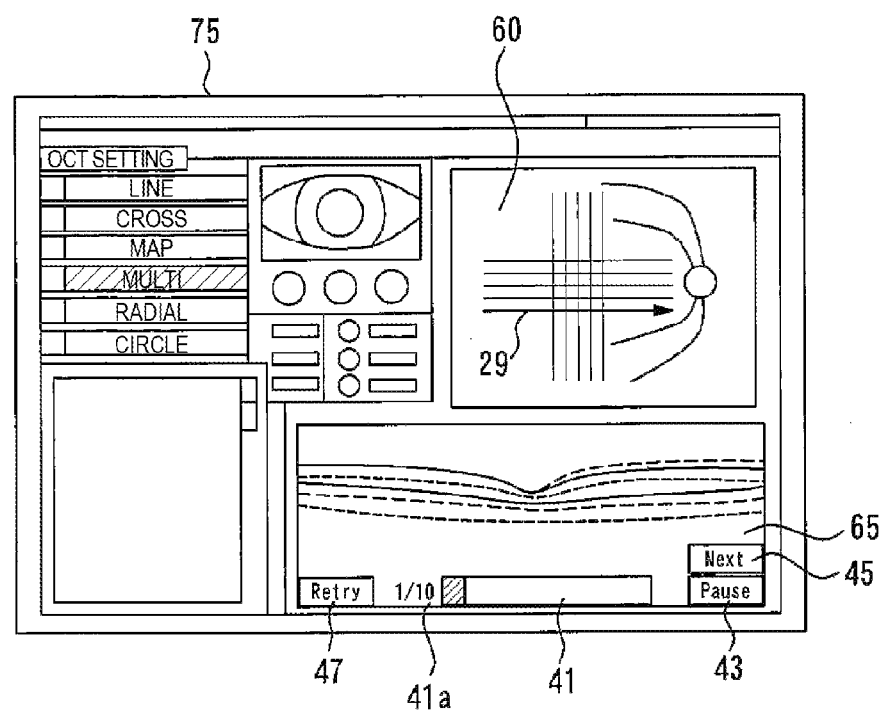
FIG. 5 illustrates an example of a photographing screen when a photographing position is changed.

For example, if the examiner operates the operation unit 74 to select the "Next" switch 45, the photographing position change signal is output. When receiving the photographing position change signal, the control unit 70 completes the photographing at the photographing position (first photographing position), as the subsequent photographing operation, even when the frame number of tomographic images in which the averaging process is set in advance is not acquired. Then, the control unit 70 changes the photographing position of the tomographic image to the subsequent photographing position (second photographing position). At this time, the averaged image acquired during the temporary stop at the photographing position in the scanning line 28 is stored in the memory 72 as the tomographic image in the scanning line 28. FIG. 5 illustrates an example of the photographing screen when the photographing position is changed. As illustrated in FIG. 5, the control unit 70 changes the photographing position of the tomographic image from the scanning line 28 to the scanning line 29. The control unit 70 starts to acquire multiple tomographic images at the photographing position in the scanning line 29. When completing the photographing at all the photographing positions, the control unit 70 completes the photographing without changing the photographing position. This configuration enables the photographing process to be transferred to the subsequent photographing position even when the photographing of the frame number of tomographic images which is set at the predetermined photographing position is not completed. Accordingly, it is possible to smoothly perform the subsequent photographing. It is particularly advantageous since it is possible to smoothly complete the photographing at the multiple photographing positions in the scan pattern for acquiring the tomographic images. Therefore, even when the photographing is not completed, if the averaged image is good to some extent, the process can be transferred to the subsequent photographing position. The examiner can easily complete the photographing without feeling stress, thereby leading to enhanced convenience.

Figure 6:
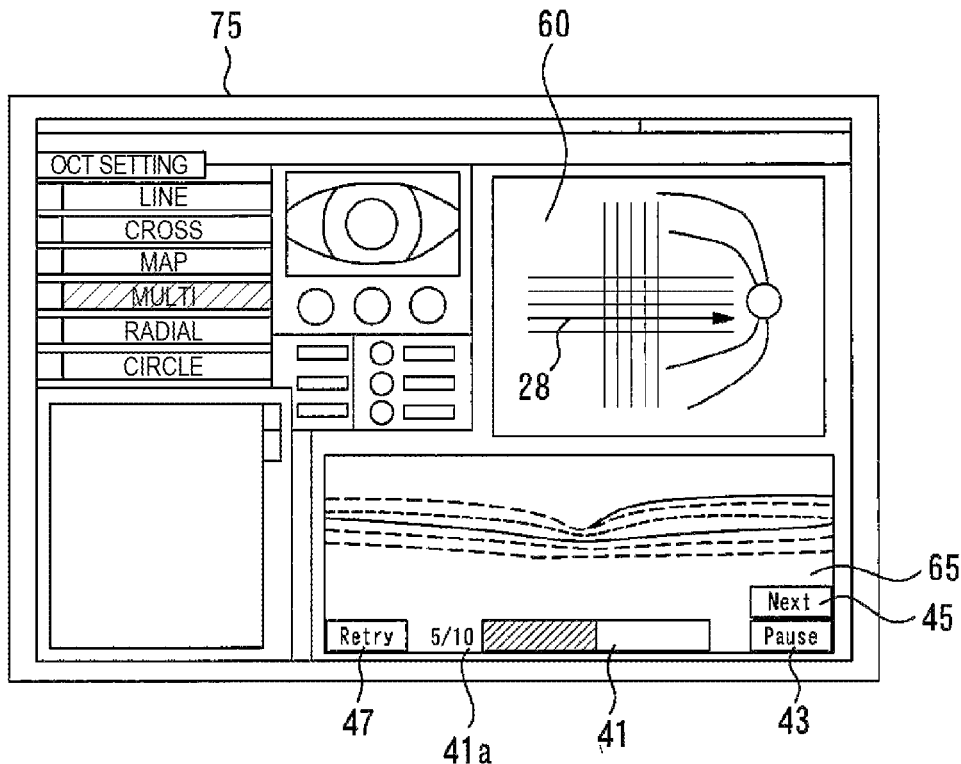
FIG. 6 illustrates an example of a photographing screen when a control for storing tomographic images restarts from a temporary stop state.

For example, if the examiner operates the operation unit 74 to select the "Restart" switch 46, the photographing restart signal is output. When receiving the photographing restart signal, the control unit 70 restarts the control for storing the tomographic images in the memory 72 at the photographing position where the tomographic image is being acquired during the temporary stop, as the subsequent photographing operation. In addition, the control unit 70 causes the memory 72 to store the tomographic images in addition to the number of acquired tomographic images stored in the memory 72 until the temporary stop signal is received. FIG. 6 illustrates an example of the photographing screen when restarting the control for storing the tomographic images from the temporary stop state. That is, as illustrated in FIG. 6, the control unit 70 restarts the photographing of the tomographic image from the temporary stop state in the scanning line 28. At this time, the frame number of tomographic images is added to the frame number in the temporary stop state, and is stored in the memory 72. For example, when the frame number of tomographic images which is stored in the memory 72 and is subjected to the averaging process until the temporary stop represents four frames, the control unit 70 stores the tomographic image to be stored in the memory 72 when restarting the photographing as the tomographic image of the fifth frame (refer to the parameter 41 and the numerical display 41a in FIG. 6). The control unit 70 changes the photographing position to the subsequent photographing position, when the tomographic images are additionally stored in the memory 72 and the frame number reaches the set frame number (for example, 10 frames in FIG. 6). This configuration enables the photographing to be restarted in the middle of the photographing of the tomographic image. Therefore, it is possible to shorten the time for acquiring the tomographic image.

Figure 7:
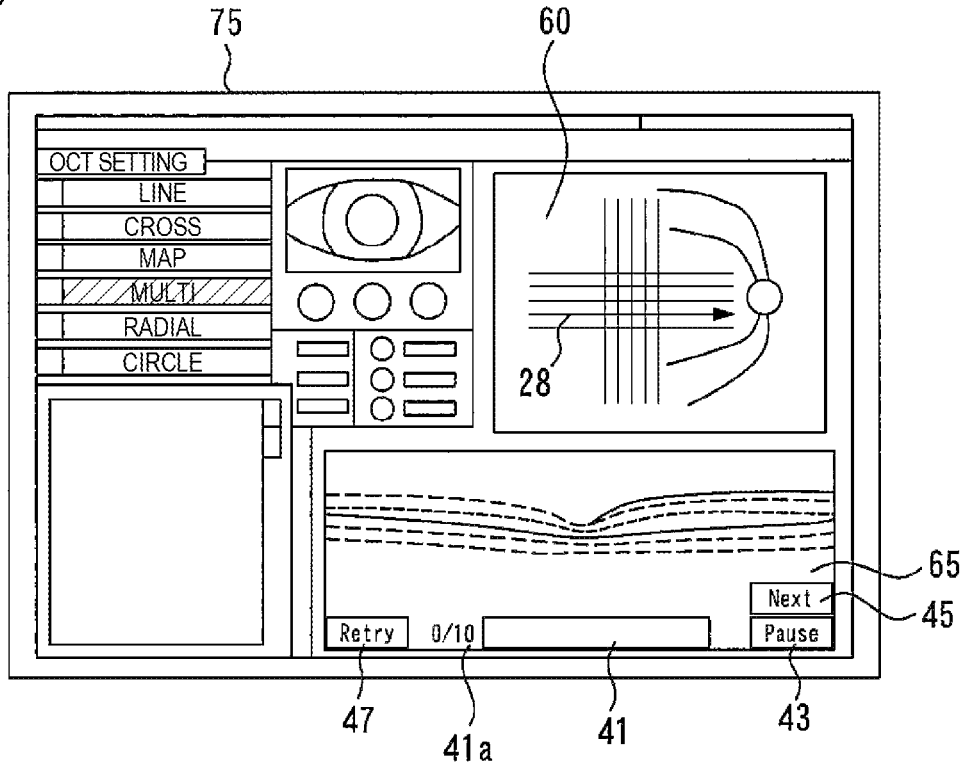
FIG. 7 illustrates an example of a photographing screen when a control for storing tomographic images restarts from a temporary stop state and photographing is performed again.

For example, if the examiner operates the operation unit 74 to select the "Retry" switch 47, a re-photographing signal is output. When receiving the re-photographing signal, the control unit 70 restarts the control for storing the tomographic images in the memory 72 at the photographing position where the tomographic image is being acquired during the temporary stop, as the subsequent photographing operation. At this time, the control unit 70 resets the acquisition number of tomographic images stored in the memory 72, and stores the tomographic images in the memory 72 again until the temporary stop. FIG. 7 illustrates an example of the photographing screen when performing the photographing again after restarting the control for storing the tomographic images from the temporary stop state. As illustrated in FIG. 7, the control unit 70 restarts the photographing of the tomographic image from the temporary stop state in the scanning line 28. At this time, the control unit 70 deletes the tomographic images stored in the memory 72 until the temporary stop. Then, the control unit 70 causes the memory 72 to store the tomographic images starting from the first frame (refer to the parameter 41 and the numerical display 41a in FIG. 7). When the control unit 70 causes the memory 72 to store the tomographic images and the frame number reaches the set frame number, the control unit 70 changes the photographing position to the subsequent photographing position. This configuration enables the photographing to be performed again from the beginning, when the tomographic image acquired until the temporary stop is not good enough (for example, when the reference image (tomographic image) for the averaging process is not good enough). Therefore, it is possible to easily acquire a good tomographic image.

In the present embodiment, even in the temporary stop state, the tracking control is continuously performed. Even during the temporary stop, the tracking control is performed. In this manner, for example, it is not necessary to re-set the photographing position when restarting the photographing of the tomographic image from the temporary stop, or when performing the photographing of the tomographic image at the subsequent photographing position. Accordingly, it is possible to smoothly transfer the process to the photographing operation. In the temporary stop state, the tracking control may be stopped. In this case, for example, the tracking control is performed based on the positional deviation between the front image stored in the memory 72 before the temporary stop and the current front image, when restarting the photographing of the tomographic image from the temporary stop state, or when performing the photographing of the tomographic image at the subsequent photographing position.

The control unit 70 sequentially acquires the tomographic image in each scanning line. If the averaged image is acquired at the photographing position in each scanning line, the control unit 70 completes the photographing.

The configuration as described above enables the tomographic image to be confirmed in the middle of the tomographic image acquisition. Accordingly, it is not necessary to confirm the acquired tomographic image after intentionally completing the photographing and transferring the photographing screen to a confirmation screen or an analysis screen. In addition, it is possible to confirm the adjustment of the photographing state or to adjust the photographing state in the middle of the photographing. Therefore, according to the present invention, it is possible to shorten a photographing period of time, and to reduce the burden on the examiner or the subject. In addition, it is possible to easily acquire an excellent tomographic image.

Modification Example

The present embodiment is configured so that the control unit 70 temporarily stops the photographing when receiving the first operation signal (for example, temporary stop signal) during the photographing operation at the set multiple photographing positions, and the control unit 70 transfers the process to the subsequent photographing operation when receiving the second operation signal (for example, photographing position change signal). However, the present embodiment is not limited thereto. The first operation signal and the second operation signal may be configured to be shared in use. In this case, when receiving the photographing position change signal during the photographing operation, the control unit 70 changes the photographing position to the subsequent photographing position without performing the temporary stop. This configuration enables the examiner to arbitrarily transfer the process to the photographing at the subsequent photographing position even when performing the photographing at the predetermined photographing position. Accordingly, it is possible to shorten the photographing period of time, and to smoothly complete the photographing. In addition, the examiner can arbitrarily adjust the photographing operation, thereby leading to enhanced convenience.

In addition, when receiving the re-photographing signal during the photographing operation, the control unit 70 may reset the acquisition number of tomographic images stored in the memory 72 without performing the temporary stop, and may cause the memory 72 to store the tomographic images again from the beginning. This configuration is advantageous to the examiner, for example, when the current photographing position deviates from the photographing position where the reference image (tomographic image) subjected to the averaging process is acquired, and thus the progress of the averaging process is not good enough. That is, since the reference image used in the averaging process is acquired again, the tomographic image acquired at the current photographing position is newly set again as the reference image. Therefore, there is no more deviation of the photographing position between the reference image and the current tomographic image, thereby improving the photographing state. This enables the photographing period of time to be shortened and the photographing to be smoothly completed.

In the present embodiment, the configuration has been described as an example where the optical scanner 108 is controlled to scan the multiple different photographing positions set on the eye by using the measurement beam, and the multiple tomographic images are acquired at each photographing position. However, the present embodiment is not limited thereto. Any configuration can be adopted as long as multiple tomographic images are acquired based on the set photographing position. For example, the present embodiment can also be applied to a case of a single scan. That is, when the present invention is applied to a case of the line scan, the control unit 70 acquires multiple tomographic images at the photographing position of the set line scan. The present invention is particularly advantageous as described above since it takes time for completing the photographing when increasing the frame number (for example, 120 frames) of tomographic images used in the averaging process.

The present embodiment is configured so that during the temporary stop, when transferring the process to the subsequent photographing position even in the middle of the photographing, the averaged image is acquired by using the tomographic image acquired until the temporary stop at the photographing position which is used in the middle of the photographing, and the averaged image is stored in the memory 72 as the photographed image. However, the present embodiment is not limited thereto. A configuration may be made so that the averaged image at the photographing position before the process is transferred to the photographing position is not stored as the photographed image when the process is transferred to the subsequent photographing position. For example, when performing the control for transferring the temporary stop state of the photographing to the subsequent photographing position, the control unit 70 does not store the tomographic image acquired at the photographing position where the photographing is performed in the temporary stop state. Then, when moving to the subsequent photographing position, the control unit 70 causes the memory 72 to delete the tomographic image acquired at the photographing position where the photographing is performed in the temporary stop state. In this case, the averaged image (tomographic image) is not acquired at the photographing position where the temporary stop is performed, out of the multiple photographing positions, after the photographing is completed. The examiner performs the re-photographing, if necessary, thereby acquiring the averaged image at the photographing position where the temporary stop is performed. This configuration enables the photographing to be performed by skipping the photographing position where the progress of the photographing is slow. Therefore, it is possible to smoothly perform the photographing.

The present embodiment may adopt a configuration where the frame number of tomographic images used in the averaging process is changed in the middle of the photographing (during the temporary stop). In this case, a configuration may be made so that the examiner can change the frame number to any desired frame number, or so that the control unit 70 automatically changes the frame number when a predetermined time elapses in the photographing time at a predetermined photographing position. This enables the photographing to be smoothly completed.

In the present embodiment, an optical tomographic photographing apparatus which photographs the eye fundus has been described as the ophthalmic photographing apparatus, but the present embodiment is not limited thereto. The present invention can also be applied to the optical tomographic photographing apparatus which photographs the tomographic image of the anterior ocular segment.

The present embodiment is not limited to the apparatus described in the present embodiment. For example, ophthalmic photographing software (program) for functioning as in the above-described embodiment may be supplied to a system or an apparatus via a network or various storage media. Then, the program can be read out and executed by a computer (for example, CPU or the like) of the system or the apparatus.

What is claimed is:

1. An ophthalmic photographing apparatus comprising:
an interference optical system configured to acquire a tomographic image of an eye, the interference optical system including an optical scanner configured to scan the eye by using a light beam emitted from a light source and a detector configured to detect an interference signal between a measurement beam and a reference beam which are emitted from the light source;
a processor; and
memory storing computer readable instructions, when executed by the processor, causing the ophthalmic photographing apparatus to:
control the interference optical system to acquire multiple tomographic images based on a photographing position set on the eye, and store the multiple tomographic images in a storage unit;
acquire a composite image by performing a composite process on the multiple tomographic images stored in the storage unit;
receive an operation signal from an operation unit;
start a photographing operation for acquiring the multiple tomographic images based on the set photographing position;
acquire the composite image from the multiple tomographic images which are acquired by the interference optical system and stored in the storage unit until a first operation signal is received from the operation unit during the photographing operation; and
transfer a process to a subsequent photographing operation when a second operation signal is received from the operation unit.

2. The ophthalmic photographing apparatus according to claim 1, wherein the computer readable instruction when executed by the processor causes the ophthalmic photographing apparatus to temporary stop storing the tomographic images in the storage unit, acquire the composite image form the multiple tomographic images stored in the storage unit and output the acquired composite image when the first operation signal is received from the operation unit during the photographing operation.

3. The ophthalmic photographing apparatus according to claim 2, wherein the subsequent photographing operation includes a process of restarting storing the tomographic images in the storage unit and a process of storing the tomographic images in addition to the acquisition number of tomographic images stored in the storage unit until the first operation signal is received.

4. The ophthalmic photographing apparatus according to claim 2, wherein the subsequent photographing operation includes a process of restating storing the tomographic images in the storage unit, a process of resetting the acquisition number of tomographic images stored in the storage unit until the first operation signal is received from the operation unit, and a process of storing the tomographic images in the storage unit again.

5. The ophthalmic photographing apparatus according to claim 1, wherein the computer readable instruction when executed by the processor causes the ophthalmic photographing apparatus to:

control the optical scanner to scan multiple different photographing positions set on the eye by using the measurement beam, acquire multiple tomographic images at each of the multiple different photographing position, and store the multiple tomographic images in the storage unit;

start the photographing operation for acquiring the multiple tomographic images respectively at the multiple photographing positions set by the image acquisition unit; and acquire the composite image from the multiple tomographic images which are acquired at a first photographing position where the interference optical system acquires the tomographic image when the first operation signal is received from the operation unit and which are stored in the storage unit until the first operation signal is received from the operation unit during the photographing operation.

6. The ophthalmic photographing apparatus according to claim 5, wherein the subsequent photographing operation includes a process of changing an acquisition position of the tomographic image from the first photographing position to a second photographing position, and a process of starting the photographing operation for acquiring the tomographic image at the second photographing position.

7. The ophthalmic photographing apparatus according to claim 6, wherein the first operation signal and the second operation signal are shared in use.

8. The ophthalmic photographing apparatus according to claim 1 further comprising:

an observation optical system configured to acquire a front image of the eye, wherein the computer readable instruction when executed by the processor causes the ophthalmic photographing apparatus to:

set the front image acquired by the observation optical system as a reference image;

detect deviation between the reference image and another front image of the eye by image processing, and acquire the multiple tomographic images at the set photographing position while controlling the drive of the optical scanner based on the detection result of the deviation.

9. An ophthalmic photographing apparatus comprising:

an interference optical system configured to acquire a tomographic image of an eye, the interference optical system including an optical scanner configured to scan the eye by using a light beam emitted from a light source and a detector configured to detect an interference signal between a measurement beam and a reference beam which are emitted from the light source;

a processor; and memory storing computer readable instructions, when executed by the processor, causing the ophthalmic photographing apparatus to:

control the interference optical system to acquire multiple tomographic images based on a photographing position set on the eye, and store the multiple tomographic images in a storage unit;

acquire a composite image by performing a composite process on the multiple tomographic images stored in the storage unit;

receive an operation signal from an operation unit;

start a photographing operation for acquiring the multiple tomographic images based on the photographing position set by the image acquisition unit;

temporary stop storing the tomographic images in the storage unit when a first operation signal is received from the operation unit during the photographing operation; and transfer a process to a subsequent photographing operation when a second operation signal is received from the operation unit.

10. The ophthalmic photographing apparatus according to claim 9, wherein the computer readable instruction when executed by the processor causes the ophthalmic photographing apparatus to:

control the optical scanner to scan multiple different photographing positions set on the eye by using the measurement beam, acquire multiple tomographic images at each of the multiple different photographing position, and store the multiple tomographic images in the storage unit;

start the photographing operation for acquiring the multiple tomographic images respectively at the multiple photographing positions set by the image acquisition unit; and temporary stop storing the tomographic images in the storage unit at a first photographing position where the interference optical system acquires the tomographic image when a first operation signal is received from the operation unit during the photographing operation, and the subsequent photographing operation includes a process of changing an acquisition position of the tomographic image from the first photographing position to a second photographing position, and a process of starting the photographing operation for acquiring the tomographic image at the second photographing position.

11. A non-transitory computer readable recording medium storing an ophthalmic photographing program that is executed by a processor of a control device which controls an operation of an ophthalmic photographing apparatus including an interference optical system configured to acquire a tomographic image of an eye, the interference optical system including an optical scanner configured to scan the eye by using a light beam emitted from a light source and a detector configured to detect an interference signal between a measurement beam and a reference beam which are emitted from the light source, and the program causing the control device to:

control the interference optical system to acquire multiple tomographic images based on a photographing position set on the eye, and store the multiple tomographic images in a storage unit;

acquire a composite image by performing a composite process on the multiple tomographic images stored in the storage unit;

receive an operation signal from an operation unit;

start a photographing operation for acquiring the multiple tomographic images based on the photographing position set by the image acquisition unit;

acquire the composite image from the multiple tomographic images which are acquired by the interference optical system and stored in the storage unit until a first operation signal is received from the operation unit during the photographing operation; and transfer a process to a subsequent photographing operation when a second operation signal is received from the operation unit.

* * * * *